(12) United States Patent
van Rens

(10) Patent No.: US 10,451,717 B2
(45) Date of Patent: Oct. 22, 2019

(54) ULTRASOUND TRANSDUCER ASSEMBLY

(71) Applicant: KONINKLIJKE PHILIPS N.V., Eindhoven (NL)

(72) Inventor: Antonia Cornelia van Rens, Nuenen (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/242,158

(22) Filed: Jan. 8, 2019

(65) Prior Publication Data

US 2019/0137612 A1     May 9, 2019

Related U.S. Application Data

(63) Continuation of application No. 15/314,301, filed as application No. PCT/EP2015/062709 on Jun. 8, 2015, now Pat. No. 10,209,352.

(30) Foreign Application Priority Data

Jun. 12, 2014 (EP) .................................... 14172046

(51) Int. Cl.
*A61B 8/00* (2006.01)
*G01S 15/89* (2006.01)
*G10K 11/34* (2006.01)
*A61B 8/08* (2006.01)
*G01S 7/52* (2006.01)

(52) U.S. Cl.
CPC ........ *G01S 7/52047* (2013.01); *A61B 8/0883* (2013.01); *A61B 8/4488* (2013.01); *G01S 7/5208* (2013.01); *G01S 15/8915* (2013.01); *G01S 15/8993* (2013.01); *G10K 11/346* (2013.01)

(58) Field of Classification Search
CPC . A61B 8/4488; A61B 8/0883; G01S 15/8993; G01S 7/52047; G01S 7/5208; G01S 15/8915; G10K 11/346
USPC .......................................................... 73/625
See application file for complete search history.

(56) References Cited

U.S. PATENT DOCUMENTS

| | | | |
|---|---|---|---|
| 4,140,022 A | 2/1979 | Maslak | |
| 4,790,320 A | 12/1988 | Perten et al. | |
| 5,544,655 A | 8/1996 | Daigle | |
| 5,676,147 A | 10/1997 | Petrofsky et al. | |
| 5,832,923 A | 11/1998 | Engeler et al. | |
| 5,908,390 A | 6/1999 | Matsushima | |
| 5,997,479 A | 12/1999 | Savord et al. | |

(Continued)

FOREIGN PATENT DOCUMENTS

EP     2944976 A1     11/2015

*Primary Examiner* — Jacques M Saint Surin

(57) ABSTRACT

An ultrasound transducer assembly is disclosed, comprising: a plurality of ultrasound transducer elements for receiving ultrasound waves and for providing transducer signals corresponding to the respectively received ultrasound waves. The assembly comprises a plurality of signal combiners for providing different output signals on the basis of the transducer signals, and a plurality of timing elements for providing different time shifts to the transducer signals. Each of the ultrasound transducer elements is connected to a plurality of the signal combiners for providing the transducer signals including the different time shifts to different of the signal combiners.

13 Claims, 6 Drawing Sheets

(56) References Cited

U.S. PATENT DOCUMENTS

| | | |
|---|---|---|
| 8,194,876 B2 | 6/2012 | Kim et al. |
| 8,298,144 B2 * | 10/2012 | Burcher ............... A61B 5/0059 |
| | | 600/407 |
| 8,690,782 B2 | 4/2014 | Colby |
| 10,209,352 B2 * | 2/2019 | van Rens ............. A61B 8/4488 |
| 2015/0025385 A1 | 1/2015 | Ikeda et al. |

* cited by examiner

ULTRASOUND TRANSDUCER ASSEMBLY

CROSS-REFERENCE TO RELATED APPLICATIONS

This application is a continuation of U.S. application Ser. No. 15/314,301, filed Nov. 28, 2016, which is the U.S. National Phase application under 35 U.S.C. § 371 of International Application No. PCT/EP2015/062709, filed Jun. 8, 2015, which claims the benefit of European Application Serial No. 14172046.6, filed Jun. 12, 2014. These applications are hereby incorporated by reference herein.

FIELD OF THE INVENTION

The present invention relates to an ultrasound transducer assembly, in particular an ultrasound beamformer for receiving ultrasound waves.

The present invention further relates to an ultrasound imaging system, in particular for in-body ultrasound imaging like cardiovascular or transesophageal echocardiography imaging.

BACKGROUND OF THE INVENTION

Ultrasound imaging systems are generally known producing real-time images of internal portions of a tissue of a human body or the like. Such imaging systems include a multiple channel transmit beamformer and a multiple channel receive beamformer either coupled to a single array of ultrasonic transducers using a transmit and receive switch or coupled separately to a transmit transducer array and a receive transducer array. The transmit beamformer generates timed electrical pulses and applies them to individual transducer elements to generate an ultrasound beam to a portion of interest to be analyzed. A portion of the acoustic energy is scattered back towards the transducer array from the tissues structures. An array of received transducers, which may be the same as the transmit transducers converts the pressure pulses into corresponding electrical pulses. The receive beamformer usually has a plurality of processing channels with compensating delay elements, wherein a delay value for each channel is selected to collect ultrasound waves from a selected area of interest or from a selected steering direction.

A corresponding ultrasound receive beamformer with phased sub-arrays is e.g. known from U.S. Pat. No. 5,676,147.

The ultrasound penetration depth and, therefore, the area of interest is inversely proportional to the resonance frequency of the ultrasound waves, so that the field of view is close to the transducer array for high ultrasound frequencies. In order to provide high quality images of a field of view, fine and precise timing delays are required for these high ultrasound frequencies. Further, parasitic system-related time delays have an increased impact on the final image quality for these frequencies.

U.S. Pat. No. 4,790,320 discloses an apparatus for parallel processing of ultrasonic information to derive simultaneously multiple vectors of ultrasonic information per ultrasonic transmission. The apparatus includes in a transducer array for each transducer element an analog to digital converter and a delay processing subsystem associated with each analog to digital converter. The output of each first incremental delay means of all of the delay processing subsystems is applied to a first summing network and, simultaneously, the output of each of the second incremental delay means is applied to a second summing network which produces a second vector of time synchronized echo information.

SUMMARY OF THE INVENTION

It is an object of the present invention to provide an improved ultrasound transducer assembly providing a higher image quality with low technical effort.

It is furthermore an object of the present invention to provide a corresponding ultrasound imaging system.

In a first aspect of the present invention, an ultrasound transducer assembly is presented that comprises:
a plurality of ultrasound transducer elements for receiving ultrasound waves and for providing transducer signals corresponding to the respectively received ultrasound waves,
a plurality of signal combiners for providing different output signals on the basis of the transducer signals, and
a plurality of timing elements for providing different time shifts to the transducer signals,
wherein each of the ultrasound transducer elements is connected to a plurality of the signal combiners for providing the transducer signals including the different time shifts to different of the signal combiners, respectively.

In a further aspect of the present invention, ultrasound imaging system is presented comprising an ultrasound transducer array including a plurality of ultrasound transducer elements for transmitting and receiving ultrasound waves and an ultrasound transducer assembly of this kind.

Preferred embodiments of the invention are defined in the dependent claims.

The present invention is based on the idea to provide an ultrasound transducer assembly having a plurality of transducer elements, wherein different transducer signals of the transducer elements are differently time shifted and provided to different signal combiners. Parasitic delays or timing errors of the transducer signals can be compensated when the different output signals of the signal combiners are combined. Hence, a time delay of the transducer signals leads to an small amplitude error of the micro-beamformed output signal of the transducer assembly but not to a steering angle error so that the image quality of the overall beamformer can be improved with low technical effort.

The plurality of ultrasound transducer elements, which are each connected to a plurality of the signal combiners form a group of first transducer elements of the ultrasound transducer assembly.

In a preferred embodiment, each of the ultrasound transducer elements is connected to a plurality of the timing elements for providing the different time shifts to each of the transducer signals. This is a possibility to achieve individual time shifts and to provide the transducer signal including the different time shifts to the different signal combiners.

In a preferred embodiment, a plurality of secondary transducer signals is formed from the transducer signal of each of the ultrasound transducer elements and wherein each of the split transducer signals is provided to one of the signal combiners, respectively. The secondary transducer signals are identical to the transducer signals and preferably formed by splitting or copying the transducer signal. Since the transducer signals of each of the transducer elements are provided to different signal combiners and since the transducer signals are differently time shifted, the timing errors and/or propagation delays included in the transducer signals can compensate each other, effectively.

In a preferred embodiment, the signal combiners each comprise an adder. This is a possibility to combine the plurality of transducer signals with a low technical effort.

In a preferred embodiment, the transducer signals of the plurality of transducer elements provided to the different signal combiners are weighted by means of different weight factors. This is a possibility to adjust the output signals combined at the signal combiners individually, since the differently time shifted transducer signals can be weighted individually. By means of the different weight factors a precise compensation of the timing errors can be achieved.

In a preferred embodiment, an amplifier or an attenuator device is associated to each of the transducer elements to provide different gain factors to the transducer signals. It shall be understood that the gain factors may be larger than one or smaller than one so that the transducer signals are either attenuated or amplified. This is a further possibility to individually set the transducer signals to an individual value so that a precise compensation of the error delays and an improved imaging can be achieved.

In a preferred embodiment, the gain factors of the transducer signals provided to one of the signal combiners having different absolute values. This is a possibility to individually set the output signal of the different signal combiners to an optimal combination of the transducer signal.

In a preferred embodiment, the ultrasound transducer assembly further comprises a second plurality of transducer elements, wherein a delay element is associated to each of the second plurality of transducer elements for providing a fixed time delay to the respective transducer signals of the second plurality of transducer elements. This is a possibility to achieve positive and negative time shifts to the individual transducer signals since a fixed time delay is provided to all transducer signals.

In a preferred embodiment, each of the second plurality of transducer elements is connected to one of the signal combiners. The second plurality of transducer elements form a second group of transducer elements of the ultrasound transducer assembly. These transducer elements can form a reference signal for the first transducer elements which are connected to two of the signal combiners.

In a preferred embodiment, the plurality of second transducer elements and the respectively connected delay elements are virtual elements. This is a possibility to reduce the technical effort, since these reference elements can be simulated including the fixed time delay.

In a preferred embodiment, the time shift provided to the transducer signals include a fixed time delay and a relative time shift. This is a possibility to individually set the time shift to positive or negative values.

In a preferred embodiment, the relative time shift of the transducer signals provided to a first of the signal combiners is a positive time shift and the relative time shift of the transducer signals provided to a second of the signal combiners is a negative time shift. This is a possibility that the timing errors of the transducer signals can compensate each other, since the relative time shift provided to the signal combiners are positive and negative time shifts of the same transducer signals.

In a preferred embodiment, the time shifts of the transducer signals provided to one of the signal combiners have different absolute values. This is a further possibility to achieve a precise compensation of the timing errors.

In a further preferred embodiment, the time shifts of the transducer signals provided to one of the signal combiners are multiples of on first time shift.

In a further preferred embodiment, the time shifts of the transducer signals provided to different of the signal combiners have different polarities.

The plurality of signal combiners are connected to each other to combine the plurality of output signals to an overall output signal of the transducer assembly. This is a possibility to achieve a single error-compensated output signal of the ultrasound transducer assembly.

In a further preferred embodiment, the plurality of ultrasound transducer elements are connected to the signal combiners in parallel to each other. This is a possibility to combine the transducer signals to different output signals so that a timing error compensation can be achieved.

As mentioned above, the ultrasound transducer assembly according to the present invention can compensate timing errors and/or parasitic delays of the transducer signals with low technical effort, since the transducer signals are individually time shifted and provided to different signal combiners, so that the timing errors are correspondingly compensated by each other in the resulting output signal. Hence, the timing errors lead only to an amplitude error of the micro-beamformed output signal but not in a steering angle error so that the image quality can be improved.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
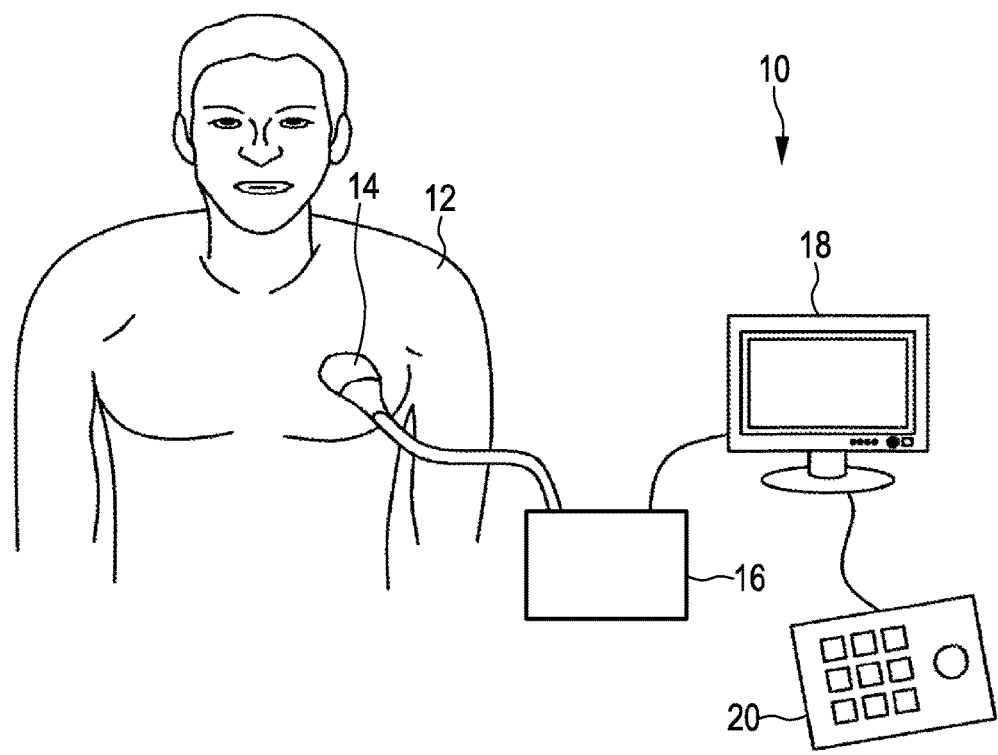
FIG. 1 shows a schematic representation of an ultrasound imaging system in use to scan a volume of a patient's body.

FIG. 1 shows a schematic illustration of an ultrasound system 10 according to an embodiment, in particular a medical three-dimensional (3D) ultrasound imaging system. The ultrasound imaging system 10 is applied to inspect a volume of an anatomical site, in particular an anatomical site of a patient 12. The ultrasound system comprises an ultrasound probe 14 having at least one transducer array having a multitude of transducer elements for transmitting and/or receiving ultrasound waves. In one example, the transducer elements each can transmit ultrasound waves in form of at least one transmit impulse of a specific pulse duration, in particular a plurality of subsequent transmit pulses. The transducer elements may be arranged in a one-dimensional array or a two-dimensional array, in particular for providing a multi-planar or three-dimensional images.

An ultrasound scan typically involves emitting ultrasound waves that illuminate a particular volume within a body, which may be designated as target volume. This can be achieved by emitting ultrasound waves at multiple different angles. A set of volume data is then obtained by receiving and processing reflected waves. A steering of the ultrasound transducer is achieved by a receive beamformer which provides individual delays to the individual ultrasound signals.

It shall be understood that the ultrasound probe 14 may either be used in a non-invasive manner (as shown in FIG. 1) or in an invasive manner (not shown) as this is usually done in two-dimensional transesophageal echocardiography (TEE). The ultrasound probe 14 may be hand-held by the user of the system, for example medical staff or a doctor. The ultrasound probe 14 is supplied to the body of the patient 12 so that an image of an anatomical site, in particular an anatomical object of the patient 12 is provided.

Further, the ultrasound system 10 may comprise a control unit 16 that controls the provision of ultrasound image via the ultrasound system 10. A control unit 16 controls the acquisition of data via the transducer array of the ultrasound probe 14 and controls the signal and image processing that form the ultrasound images out of the echos of the ultrasound beams received by the transducer array of the ultrasound probe 14.

The ultrasound system 10 may further comprise a display 18 for displaying the 3D images to the user. Still further, an input device 20 may be provided connected to the display 18 or directly to the control unit 16.

The ultrasound system 10 comprises in general a beamformer, which is provided for steering the transducer elements to a focal point within the anatomical site to be inspected. The individual transducer elements are steered to the focal point by providing individual time delays to the transducer signals so that the transit time of the ultrasound waves from the focal point to the different transducer elements can be compensated. By means of these individual time delays provided by the beamformer, a steered ultrasound transducer can be provided.

The beamformer comprises a micro-beamformer, which is located in the ultrasound probe 14 close to the transducer array. The beamformer may further comprise a system-beamformer integrated in the control unit 16 and connected to the micro-beamformer for coarse beamforming. The ultrasound system 10 further comprises an analog-to-digital converter (ADC), which is preferably connected between the micro-beamformer and the system-beamformer.

Figure 2:
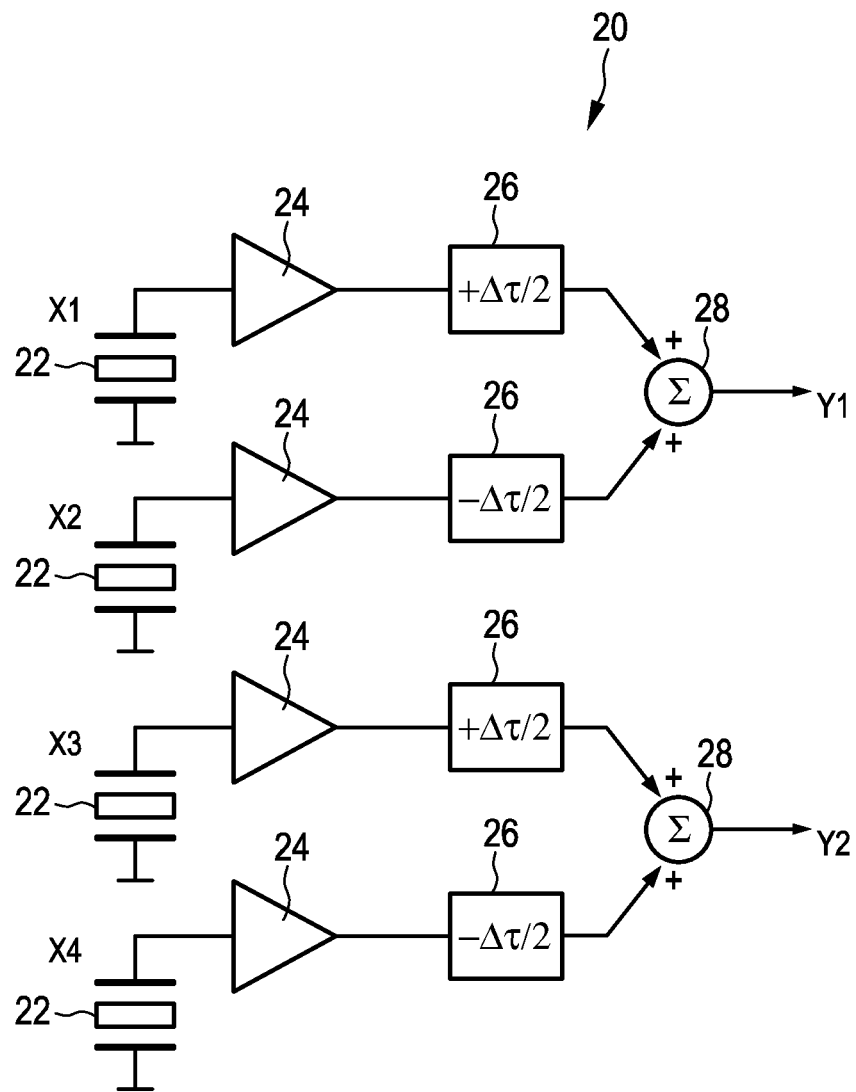
FIG. 2 shows a schematic block diagram of a known two-to-one channel receive beamformer of an ultrasound system.

FIG. 2 shows an ultrasound transducer known from the prior art which is generally denoted by 20. The ultrasound transducer 20 comprises a two-to-one channel receive micro-beamformer which is adapted to reduce the effects of timing errors by combining differently time shifted signals. The ultrasound transducer 20 comprises a plurality of transducer elements 22, which are adapted to receive ultrasound waves and to transform the ultrasound waves into an electrical transducer signal X1-X4. The transducer elements 22 are each connected to an amplifier 24 for amplifying the electrical transducer signals X1-X4, wherein the amplifiers 24 are preferably formed as operational amplifiers. The transducer elements 22 are each further connected to a timing element 26, which are adapted to provide a defined time shift to the electrical signals X1-X4 received from the transducer elements 22. Two of the transducer elements 22 are connected to one signal adder 28 in order to combine the electrical signals to one output signal Y1, Y2 which are combined by a coarse beamformer to an overall output signal of the ultrasound transducer (not shown).

The timing elements 26, which are connected to one of the signal adders 28 are adapted to provide a positive and a negative time shift to the electrical transducer signals X1-X4, respectively, so that timing errors can be compensated at the signal adder 28. In practice, all timing elements 26 provide a fixed positive time delay to the electrical transducer signals X1-X4 and the additional relative time shift so that a positive and a negative time shift can be implemented.

The disadvantage of these standard two-to-one channel receive beamformers is that the time delay must be set very precisely and that a grating lobe is generated already for moderate timing errors so that the resulting image quality is affected.

Figure 3:
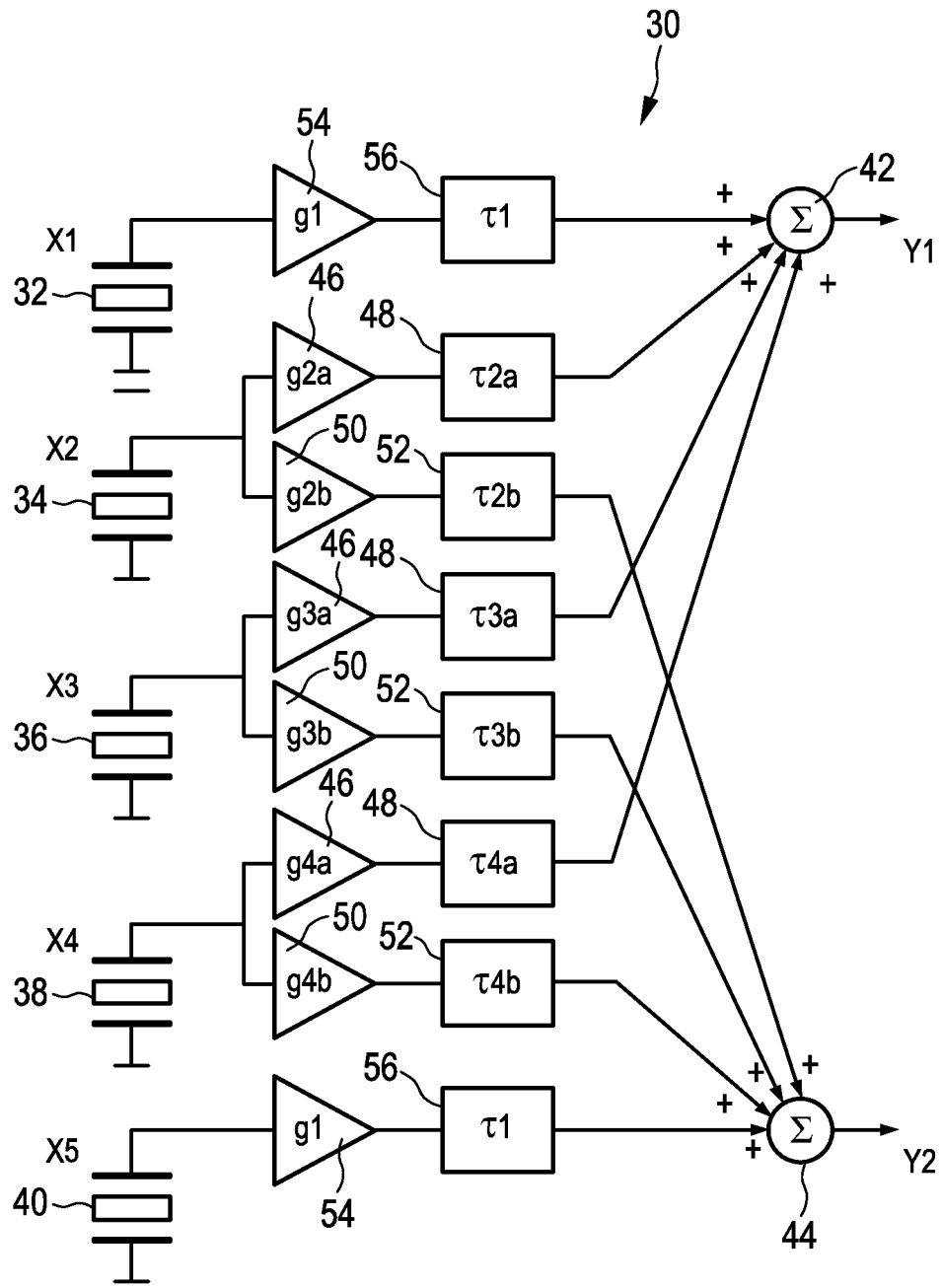
FIG. 3 shows an embodiment of a receive beamformer for timing error compensation.

FIG. 3 shows an ultrasound transducer assembly according to one embodiment of the present invention which is generally denoted by 30. The ultrasound transducer assembly 30 comprises a plurality of transducer elements 32, 34, 36, 38, 40 for receiving ultrasound waves and for providing electrical transducer signals, which are generally denoted by X1, X2, X3, X4, X5. The ultrasound transducer assembly 30 further comprises in general an ultrasound beamformer connected to the ultrasound transducer elements 32-40. The ultrasound beamformer shown in FIG. 3 is formed as a four-to-one channel micro-beamformer. The ultrasound beamformer provides steering and focussing of the ultrasound transducer elements 32-40 to a point by providing a time shift to the electrical transducer signals X1-X5 as described in the following. The ultrasound transducer elements 32-40 may be arranged in a one-dimensional or a two-dimensional array of transducer elements in order to provide a two-dimensional or a three-dimensional ultrasound image.

The ultrasound transducer assembly 30 and in particular the ultrasound micro-beamformer comprises a first signal combiner 42 and a second signal combiner 44 which provide a first output signal Y1 and a second output signal Y2. The signal combiners 42, 44 are formed as signal adders which combine electrical signals on the basis of the ultrasound transducer signals X1-X4 and X2-X5 to form the output signals Y1, Y2. The signal combiners 42, 44 are each connected to the transducer elements 34, 36, 38 so that the transducer elements 34, 36, 38 are connected in parallel to each other.

The transducer elements 34, 36, 38, which form a first group of transducer elements are each connected via a first gain element 46 and a first timing element 48 to the first adder 42. The transducer elements 34, 36, 38 are further connected via a second gain element 50 and a second timing element 52 to the second signal combiner 44. A plurality—in this case—two secondary ultrasound signals are formed of the ultrasound transducer signals X2, X3, X4 preferably by splitting or copying the ultrasound transducer signals X2, X3, X4 and the secondary signals are provided with a gain factor g by means of the gain elements 46, 50 to the timing elements. The secondary ultrasound signals are identical to the respective ultrasound transducer signals X2, X3, X4. The secondary transducer signals are further provided with a time shift τ by means of the timing elements 48, 52. The gain elements 46, 50 and the timing elements 48, 52 provide different gain factors and different time shifts τ to the ultrasound transducer signals X2-X4 corresponding to the position of the respective transducer element 34-36 and corresponding to which of the signal combiners 42, 44 the respectively gained and time shifted signal is provided.

The transducer elements 32, 40 are each connected via a gain element 54 and a timing element 56 to only one of the signal combiners 42, 44. The transducer elements 32, 40, which are respectively connected to one of the signal combiners 42, 44 belong to a second group of transducer elements. The gain elements 54 provide a reference gain to the respective ultrasound transducer signal X1, X5 and the timing elements 56 provide a fixed time delay τ1 to the ultrasound transducer signal X1, X5. The first and the second timing elements 48, 52 each provide the fixed delay τ1 to the respective ultrasound transducer signal X2, X3, X4 and an additional time shift, which is positive in the case of the first timing elements 48 and negative in the case of the second timing elements 52. Hence, the signals provided to the first signal combiner 42 have a negative time shift relative to the fixed time delay τ1 and the signals provided to the second signal combiner 44 have a positive time shift with respect to the fixed delay τ1. The output signals Y1, Y2 are finally combined e.g. by the system-beamformer to an overall output signal (not shown) of the transducer assembly 30.

The signals provided to the signal combiners 42, 44 may be provided with a weight factor in order to weigh the respective signals individually so that the respective individual transducer signals X1-X5 have an individual influence on the wave form of the output signals Y1, Y2.

Due to the combination of the differently time shifted and differently weighted ultrasound transducer signals X1-X5 combined by different signal combiners 42, 44, the resulting overall output signal is less sensitive to timing errors on the programmed delay profiles than the ultrasound beamformers known from the prior art.

The gain factors g and the time shifts τ of the gain elements 46, 50, 54 and the timing elements 48, 52, 56 have different values. The time shifts and the gain factors primarily are:

$$\tau 1 = \text{fixed delay,}$$
sufficiently large to make all delays effectively positive
$$\tau 2a = \tau 1 - \Delta\tau$$
$$\tau 2b = \tau 1 + (N-1)\Delta\tau$$
$$\tau 3a = \tau 1 - 2\Delta\tau$$
$$\tau 3b = \tau 1 + (N-2)\Delta\tau$$
$$\tau 4a = \tau 1 - 3\Delta\tau$$
$$\tau 4b = \tau 1 + (N-3)\Delta\tau$$
$$g1 = \text{reference gain}$$
$$g2a = (N-1)/N * g1$$
$$g2b = 1/N * g1$$
$$g3a = (N-2)/N * g1$$
$$g3b = 2/N * g1$$
$$\ldots$$
$$gNa = 1/N * g1$$
$$gNb = (N-1)/N * g1,$$

wherein Δτ is the incremental correction for the calculated signal propagation delay difference and N is the number of transducer elements 32-38 in a sub-channel, in this example N=4. The structure can be used to provide any N-to-1 channel receive beamformer with N being any natural number larger than one.

In a certain embodiment, the ADC may be integrated in the micro-beamformer and connected between the transducer elements and the gain elements 54, 46, 50. In a certain embodiment, the ADC is preceeded by a low noise amplifier with a fixed gain for all channels.

In a further embodiment, the transducer elements 32, 40 of the second group of elements which are only connected to one of the signal combiners 42, 44 can be implemented as virtual transducer elements, wherein the fixed time delay of the first group of transducer elements are aligned to the fixed time delay of the virtual transducer elements.

In this case, the time shifts and the gain factors will primarily be:

$$\tau 1 = \text{fixed delay,}$$
sufficiently large to make all delays effectively positive
$$\tau 2a = \tau 1 - 0.5 * \Delta\tau$$
$$\tau 2b = \tau 1 + (N - 0.5)\Delta\tau$$
$$\tau 3a = \tau 1 - 1.5\Delta\tau$$
$$\tau 3b = \tau 1 + (N - 1.5)\Delta\tau$$
$$\tau 4a = \tau 1 - 2.5\Delta\tau$$
$$\tau 4b = \tau 1 + (N - 2.5)\Delta\tau$$
$$g1 = \text{reference gain}$$
$$g2a = (N)/(N+1) * g1$$
$$g2b = 1/(N+1) * g1$$
$$g3a = (N-1)/(N+1) * g1$$
$$g3b = 2/(N+1) * g1$$
$$\ldots$$
$$gNa = (1)/(N+1) * g1$$
$$gNb = (N)/(N+1) * g1$$

wherein Δτ is the incremental correction for the calculated signal propagation delay difference and N is the number of non-virtual (real) transducer elements 34, 36, 38 in a sub-channel (in this example, N=3).

Figure 4:
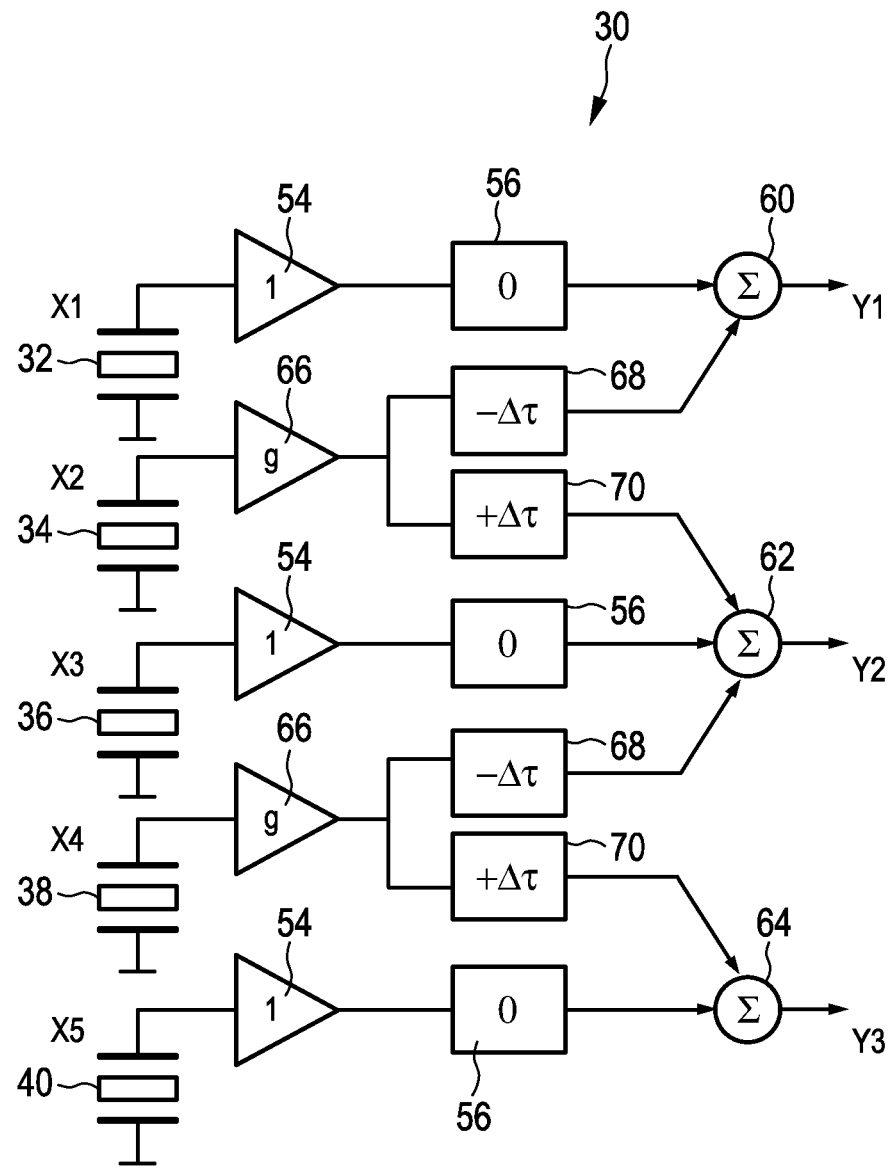
FIG. 4 shows a further embodiment of a two-to-one channel receive beamformer for timing error compensation.

FIG. 4 shows an embodiment of the ultrasound transducer assembly 30 including a two-to-one channel micro-beamformer. In this embodiment, the ultrasound transducer assembly 30 comprises three or more signal combiners 60, 62, 64, which combine signals based on the ultrasound transducer signals X1-X5 of two or three transducer elements 32-40. The signal combiners 60, 62, 64 are preferably formed as signal adders and provide the output signals Y1, Y2, Y3 of the micro-beamformer which are combined to an overall output signal by the (coarse) system—beamformer (not shown). In this embodiment, the transducer elements 32, 36, 40, which belong to the second group of transducer elements are connected via the gain element 54 and the timing element 56 directly to one of the signal combiners 60, 62, 64, respectively. The transducer elements 34, 38, which belong to the first group of transducer elements are connected to a gain element 66 for providing a gain factor g to the respective ultrasound transducer signal X2, X4, wherein two separate secondary transducer signals are formed from the ultrasound transducer signals X2, X4 including the gain factor g. The secondary transducer signals are formed by splitting or copying the transducer signals X2, X4, wherein the secondary transducer signals are identical with the secondary transducer signals except for the gain factor. The two secondary transducer signals are time shifted by means of a first timing element 68 and a second timing element 70, respectively, wherein the two secondary transducer signals are provided to different of the signal combiners 60, 62, 64.

Consequently, the transducer elements 32, 36, 40 which belong to the second group of transducer elements and which are in this row the odd transducer elements are directly connected to one of the signal combiners 60, 62, 64 and the transducer elements 34, 38 which are the even transducer elements are connected to two of the signal combiners 60, 62, 64.

As described above, the timing elements 56 provide a fixed delay τ1 to the respective ultrasound transducer signal X1, X3, X5 and the timing elements 68, 70 provide the fixed delay τ1 and additionally a relative time shift −Δτ, +Δτ to the ultrasound transducer signals X2, X4, wherein the timing element 68 provide a negative time shift −Δτ and the timing element 70 provide a positive time shift +Δτ to the respective ultrasound transducer signal X2, X4.

Since the ultrasound transducer signals X2, X4 are differently time shifted and gained by means of the gain factor g, the overall output signal is less sensitive to timing errors on the programmed delay profiles than the beamformer known from the prior art so that a more precise steering and a more precise imaging of the transducer assembly can be achieved.

In a certain embodiment, the ADC may be integrated in the micro-beamformer and connected between the transducer elements and the gain elements 54, 56 (in practice, the ADC will be preceded by a low noise amplifier with a fixed gain for all channels in this case)

Figure 5:
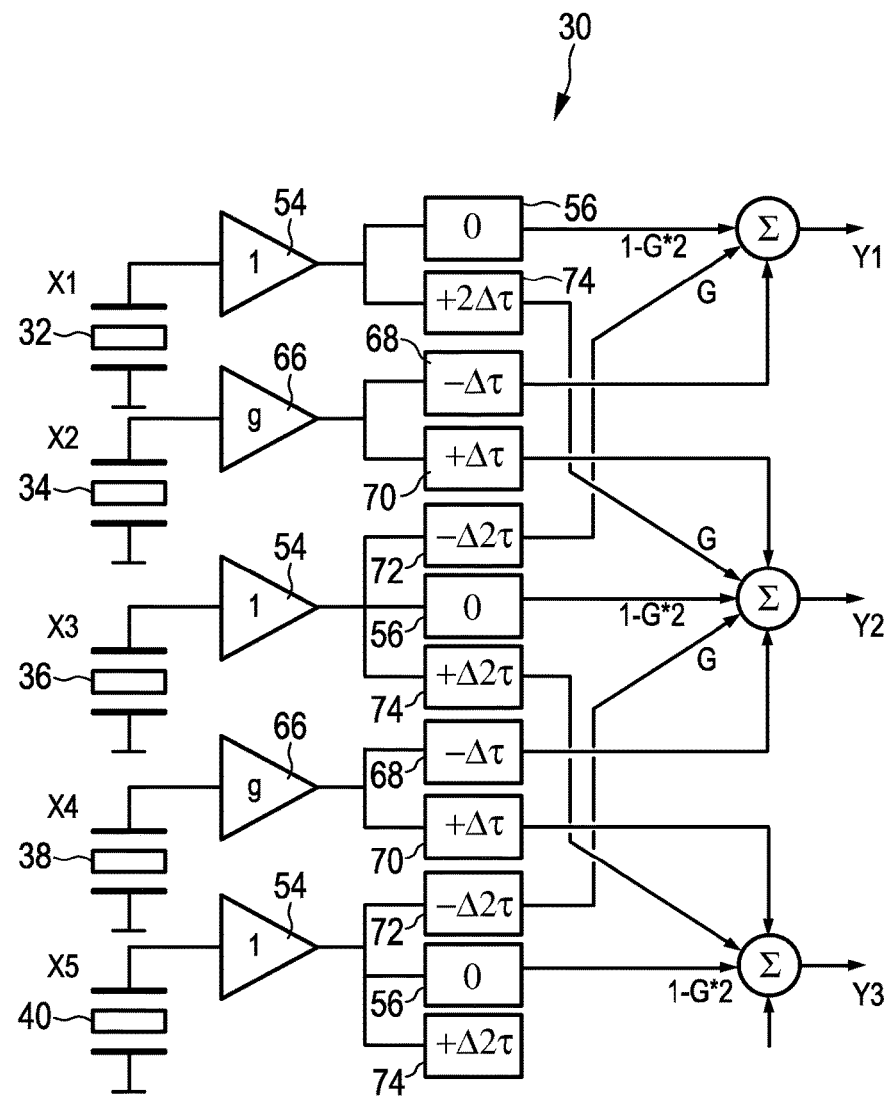
FIG. 5 shows a further embodiment of a two-to-one channel receive beamformer.

FIG. 5 shows a further embodiment of the ultrasound transducer assembly 30. In this embodiment, the transducer assembly 30 comprises the three or more signals combiners 60, 62, 64 which receive each signals on the basis of different ultrasound transducer signals X1-X5 provided by the different ultrasound transducer elements 32-40.

Identical with the embodiment of FIG. 4, the ultrasound transducer signals X2, X4 of the ultrasound transducer elements 34, 38 are provided with a gain factor g and split into two split signals, which are differently time shifted (positive and negative) by means of the timing elements 68, 70 and provided to the respectively neighbored signal combiner 60, 62, 64.

The ultrasound transducer signals X1, X3, X5 of the ultrasound transducer elements 32, 36, 40 are provided with a gain factor g by means of the gain element 54 and split into two or three split signals, wherein one split signal is provided with the fixed time delay by means of the timing element 56 and the so delayed signal is provided to one of the signal combiners 60, 62, 64. The other split signals are time shifted by means of a first timing element 72 and a second timing element 74, wherein the so differently time shifted signals are provided to different of the signal combiners 60, 62, 64. The first timing elements 72 provide the fixed time delay τ and a negative time shift to the respective split signal and the second timing elements 74 provide the fixed delay τ and a positive time shift to the split signal. In this certain embodiment, three secondary transducer signals are formed of the ultrasound transducer signals X3, X5 by splitting or copying and provided with different time shifts to three of the signal combiners, wherein the ultrasound transducer signals X2, X4 are split into two split signals and provided with different time shifts to two of the signal combiners 60, 62, 64.

Additionally the split signals are weighted by means of weight factors (G, 1-2G) at the signal combiners 60, 62, 64 in order to individually form the output signals Y1, Y2, Y3 on the basis of the ultrasound transducer signals X1-X5. Since the signals of three or more transducer elements 32-40 are combined at the signal combiners 60, 62, 64, the micro-beamformer output signal provided by this embodiment of the ultrasound transducer assembly is less sensitive to timing errors on the programmed delay profiles than a simple two-to-one channel micro-beamformer.

In a certain embodiment, the ADC may be integrated in the micro-beamformer and connected between the transducer elements and the gain elements 54, 66 and in practice, the ADC is preferably preceded by a low noise amplifier with a fixed gain for all channels in this case.

In the following, the amplitude of grating lobes of the overall output signal of the ultrasound transducer assembly 20 of FIG. 2 and the ultrasound transducer assemblies 30 of FIGS. 4 and 5 are calculated in order to determine the sensitivity to programmed timing errors.

In practice the generated micro-beamformer delay will not be exactly equal to the desired delay. The difference between the two delays is Δτ_error:

$$+\Delta\tau\_gen = +\Delta\tau + \Delta\tau\_error$$

$$-\Delta\tau\_gen = -\Delta\tau - \Delta\tau\_error$$

Note that it is assumed that the error on the positive delay is equal in magnitude but with a negative sign relative to the error on the negative delay. This is realistic since the delays are generated on the same ASIC using the same type of circuitry.

It is assumed that the ultrasound reflections of the two transducer elements can be modeled by a narrowband signal around the resonance frequency $\omega_{RES}$ according to:

$$X1(t) = A(t - \Delta\tau\_real/2) * \sin(\omega_{RES}(t - \Delta\tau\_real/2))$$

$$X2(t) = A(t + \Delta\tau\_real/2) * \sin(\omega_{RES}(t + \Delta\tau\_real/2))$$

With +Δτ_real=signal propagation delay difference of ultrasound signals X1 and X2 for the actual reflection and +Δτ if the actual reflection arrives from the steering and focusing direction A(t)=amplitude of the envelope as a function of time.

The output signal Y1_1 of the ultrasound transducer assembly shown in FIG. 2 (prior art) can be described as follows:

$$\begin{aligned}
Y1\_1(t) &= X1(t + \Delta\tau\_gen/2) + X2(t - \Delta\tau\_gen/2) \\
&= A(t - \Delta\tau\_real/2 + \Delta\tau\_gen/2) * \sin(\omega_{RES}(t - \Delta\tau\_real/2 + \\
&\quad \Delta\tau\_gen/2)) + A(t + \Delta\tau\_real/2 - \Delta\tau\_gen/2) * \\
&\quad \sin(\omega_{RES}(t + \Delta\tau\_real/2 - \Delta\tau\_gen/2))
\end{aligned}$$

For acoustic energy coming from the steering direction (Y1_1s), this formula can be rewritten to:

$$\begin{aligned}
Y1\_1s(t) &= A(t + \Delta\tau\_error/2) * \sin(\omega_{RES}(t + \Delta\tau\_error/2)) + \\
&\quad A(t - \Delta\tau\_error/2) * \sin(\omega_{RES}(t - \Delta\tau\_error/2)) \\
Y1\_1s(t) &\approx A(t) * 2 * \cos(\Delta\tau\_error/2) * \sin(\omega_{RES}t) \\
&\approx A(t) * (2 - (\omega_{RES}\Delta\tau\_error/2)^2) * \sin(\omega_{RES}t)
\end{aligned}$$ (eq. 1)

For acoustic energy coming from the direction that causes the first grating lobe (Y1_1g), this formula can be rewritten to:

$$Y1\_1g(t) = A(t + \Delta\tau\_\text{error}/2) * \sin(\omega_{RES}(t + \Delta\tau\_\text{error}/2)) - \quad \text{(eq. 2)}$$
$$A(t - \Delta\tau\_\text{error}/2 + T/2) * \sin(\omega_{RES}(t - \Delta\tau\_\text{error}/2))$$
$$Y1\_1g(t) \approx A(t) * 2 * \sin(\Delta\tau\_\text{error}/2) * \cos(\omega_{RES} t)$$
$$\approx A(t) * \Delta\tau\_\text{error} * \cos(\omega_{RES} t)$$

In case of the ultrasound transducer 30 shown in FIG. 4, the beamformer is transparent to all odd (even) transducer signals. The even (odd) signals are transferred to two signal combiners. E.g. the signal of transducer element X2 is visible in outputs Y1 and Y2 according to:

$$Y1\_2(t) = \text{gain} * A(t - \Delta\tau\_\text{gen}) * \sin(\omega_{RES}(t - \Delta\tau\_\text{gen}))$$
$$Y2\_2(t) = \text{gain} * A(t + \Delta\tau\_\text{gen}) * \sin(\omega_{RES}(t + \Delta\tau\_\text{gen})) \quad \text{(eq. 3)}$$

Typically gain factors (gain) are 0.5 . . . 0.6. In the system beamformer (not shown) the signals are combined according to:

$$Y\text{total}\_2(t) = Y1\_2(t + \Delta\tau\_\text{sys}) + Y1\_2(t - \Delta\tau\_\text{sys}) \quad \text{(eq. 4)}$$

wherein $\Delta\tau\_\text{sys}$ is the delay generated in the system beamformer, located externally in the imaging system. It is assumed that this system generates the correct steering or focusing delays (the system beamformer typically has much more calculation power than the micro-beamformer), so $$+\Delta\tau\_\text{sys} = +\Delta\tau = +\Delta\tau\_\text{gen} - \Delta\tau\_\text{error}$$
$$-\Delta\tau\_\text{sys} = -\Delta\tau = -\Delta\tau\_\text{gen} + \Delta\tau\_\text{error}$$

Rewriting equation 3 and 4 gives:

$$Y\text{total}\_2(t) = \text{gain} * (A(t - \Delta\tau\_\text{error}) * \sin(\omega_{RES}(t - \Delta\tau\_\text{error})) + A(t + \Delta\tau\_\text{error}) * \sin(\omega_{RES}(t + \Delta\tau\_\text{error}))) \approx \text{gain} * 2 * A(t) * \cos(\omega_{RES} \cdot \Delta\tau\_\text{error}) * \sin(\omega_{RES} * t) \quad \text{(eq. 5)}$$

Now it is possible to calculate the effective contribution of odd and even transducer signals provided by the first and second group of transducer elements to the output:

$$Y12\_2(t) = X1(t - \Delta\tau\_\text{real}/2 + \Delta\tau\_\text{sys}/2) + Y\text{total}2(t + \Delta\tau\_\text{real}/2 - \Delta\tau\_\text{sys}/2)$$

For acoustic energy coming from the steering direction (Y12_2s), this formula can be reduced to:

$$Y12\_2s(t) \approx A(t) * (1 + g * 2 * \cos(\omega_{RES} \Delta\tau\_\text{error})) * \sin(\omega_{RES} t) \approx \quad \text{(eq. 6)}$$
$$A(t) * (2 - 0.5 * (\omega_{RES} \cdot \Delta\tau\_\text{error})^2) * \sin(\omega_{RES} t); [g = 0.5]$$

For acoustic energy coming from the direction that causes the first grating lobe (Y12_2g), the formula can be rewritten to:

$$Y12\_2g(t) \approx A(t) * (1 - \text{gain} * 2 * \cos(\omega_{RES} \Delta\tau\_\text{error}) * \sin(\omega_{RES} t) \approx \quad \text{(eq. 7)}$$
$$A(t) * 0.5 * (\omega_{RES} \Delta\tau\_\text{error})^2 * \sin(\omega_{RES} t); -- [g = 0.5]$$

Eq. 7 shows that the amplitude of the grating lobes of the proposed ultrasound transducer including the beamformer for moderate timing errors is lower than the amplitude of the grating lobes of the standard beamformer (eq. 2). Timing errors result into a phase error between odd and even ultrasound signals in case of the standard micro-beamformer while timing errors result into an amplitude error for the proposed micro-beamformer. As all timing errors result into a reduced amplitude of the split or copied secondary transducer signals (eq. 5), it is attractive for imaging performance to choose gain factor gain>0.5, e.g. g=[0.5 . . . 0.6].

In case of the second embodiment of the proposed ultrasound transducer 30 shown in FIG. 5, the effect of the timing error is further reduced. Processing of the even transducer signals remains the same, typical value for gain g=0.5. The beamformer remains transparent for a major fraction of the odd signals.

A small fraction of the odd signals is transferred to neighbor output nodes. For example, the signal of transducer element X3 is visible in output Y1, Y2 and Y3 according to:

$$Y1\_3(t) = G * A(t - 2\Delta\tau\_\text{gen}) * \sin(\omega_{RES}(t * 2 \cdot \Delta\tau\_\text{gen})) \quad \text{(eq. 8)}$$
$$Y2\_3(t) = (1 - 2 * G) * A(t) * \sin(\omega_{RES} t)$$
$$Y2\_3(t) = G * A(t + 2\Delta\tau\_\text{gen}) * \sin(\omega_{RES}(t + 2\Delta\tau\_\text{gen}))$$

Typically gain factor g=0.5 and G=0.1667. In the system beamformer in imaging system (not shown) the signals are combined again according to:

$$Y_{total}3(t) = Y1\_3(t + 2\Delta\tau\_\text{sys}) + Y2\_3(t) + Y1\_3(t - 2 \cdot \Delta\tau\_\text{sys}) \quad \text{(eq. 9)}$$

wherein $\Delta\tau\_\text{sys}$ is the incremental delay generated in the system beamformer, located externally in the imaging system. It is assumed that this system generates the correct steering or focusing delays:

$$+\Delta\tau\_\text{sys} = \Delta\tau = +\Delta\tau\_\text{gen} - \Delta\tau\_\text{error}$$
$$-\Delta\tau\_\text{sys} = -\Delta\tau = -\Delta\tau\_\text{gen} + \Delta\tau\_\text{error}$$

Rewriting equation 8 and 9 gives:

$$Y\text{total}\_3(t) = G * (A(t - 2\Delta\tau\_\text{error}) * \sin(\omega_{RES}(t - 2\Delta\tau\_\text{error})) + \quad \text{(eq. 10)}$$
$$(1 - 2G) * A(t) * \sin(\omega_{RES} t) +$$
$$G * (A(t + 2\Delta\tau\_\text{error}) * \sin(\omega_{RES}(t + 2\Delta\tau\_\text{error}))$$
$$\approx A(t) * (1 + G * 2 * (\cos(\omega_{RES} 2\Delta\tau\_\text{error}) - 1)) *$$
$$\sin(\omega_{RES} t)$$

Now it is possible to calculate the effective contribution of odd and even signals to the output:

$$Y12\_3(t) = Y\text{total}\_3(t - \Delta\tau\_\text{real}/2 + \Delta\tau\_\text{sys}/2) + Y\text{total}\_2(t + \Delta\tau\_\text{real}/2 - \Delta\tau\_\text{sys}/2)$$

For acoustic energy coming from the steering direction (Y12_3s), this formula can be reduced to:

$$Y12\_3s(t) \approx A(t) * (1 + G * 2 * (\cos(\omega_{RES} 2\Delta\tau\_\text{error}) - 1) + \quad \text{(eq. 11)}$$
$$\text{gain} * 2 * \cos(\omega_{RES} \Delta\tau\_\text{error})) * \sin(\omega_{RES} t)$$
$$\approx A(t) * (2 - 1.2 * (\omega_{RES} \cdot \Delta\tau\_\text{error})^2) * \sin(\omega_{RES} t);$$
$$[g = 0.5, G = 0.1667]$$

For acoustic energy coming from the direction that causes the first grating lobe (Y12_3g), the formula can be rewritten to:

$$Y12\_2g(t) \approx A(t) * (1 + G * 2 * (\cos(\omega_{RES} 2\Delta\tau\_\text{error}) - 1) - \quad \text{(eq. 12)}$$

$$\text{gain} * 2 * \cos(\omega_{RES}\Delta\tau\_\text{error})) * \sin(\omega_{RES} t)$$

$$< \approx A(t) * 0.1 * (\omega_{RES}\Delta\tau\_\text{error})^2 * \sin(\omega_{RES} t);$$

$$[g = 0.5, G = 0.1667]$$

From equation 12 it is clear that the grating lobes are less dependent on the timing error and, therefore, the ultrasound transducer assembly 30 is less sensitive for timing errors in general.

Figure 6:
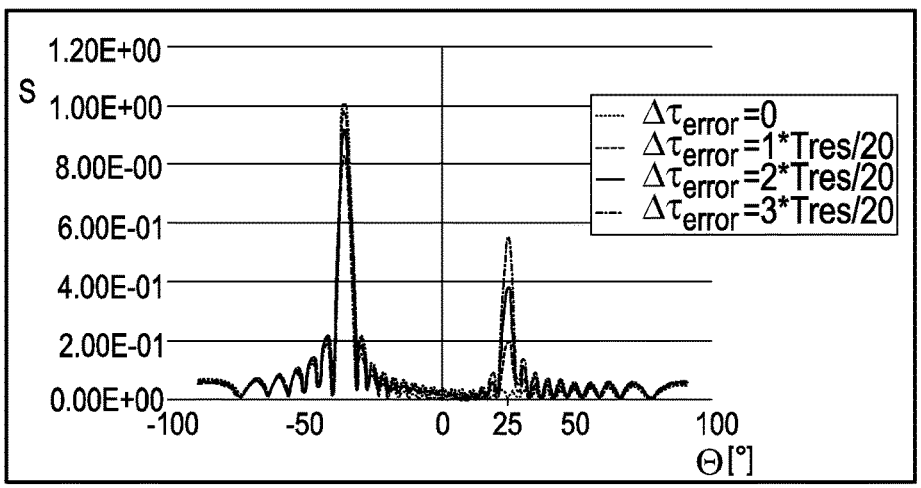
FIG. 6 shows different sensitivity diagrams for different receive beamformers and different timing errors.
Figure 6:
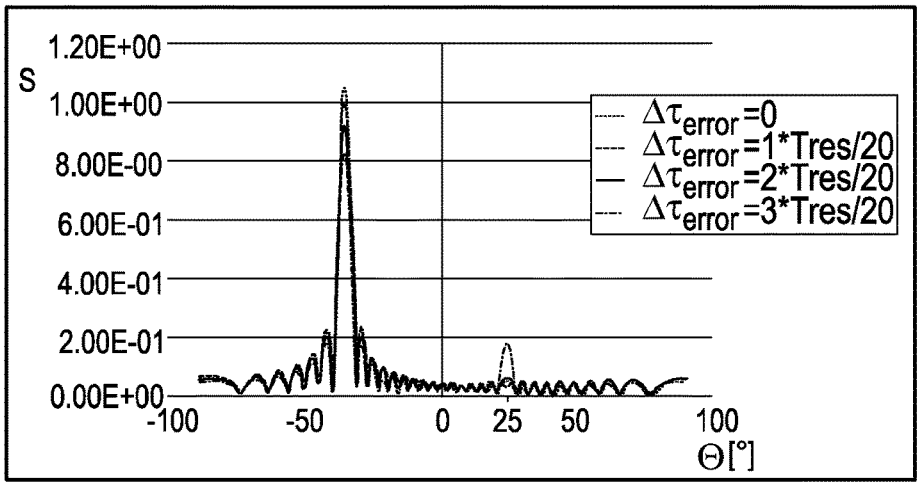
Figure 6:
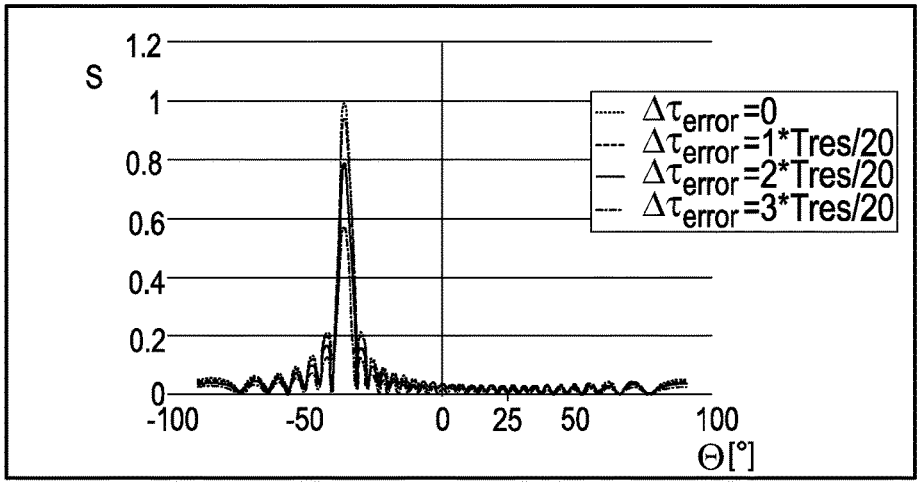

In FIG. 6a-c, the angle sensitivity of the ultrasound transducer assembly 20, 30 of FIGS. 2, 4 and 5 are shown for different values of the timing error. The sensitivity is calculated for a steering angle of −36° and a grating lobe is generated at an angle of +25°.

All cases refer to far field sensitivity of the transducer array including the respective ultrasound beamformer. Course delays have been programmed so that the beam is steered to an angle of −36°. The simulated sensitivity is shown for beamformer timing errors of $0.1*T_{res}/20$, $0.2*T_{res}/20$ and $3*T_{res}/20$ wherein $T_{res}$ is the period time of the transducer resonance frequency.

As shown in FIG. 6a, the sensitivity of the transducer assembly 20 shown in FIG. 2 including the standard two-to-one beamformer has no grating lobe for zero timing error while the amplitude of the first grating lobe (happening at +25 degrees) increases for increasing timing errors.

FIG. 6b is a simulation of the ultrasound transducer assembly shown in FIG. 4, wherein the grating lobe at 25° is merely visible for a timing error of $3*T_{res}/20$. For smaller timing errors, the grating lobe amplitude reduces rapidly.

FIG. 6c shows a simulation of the sensitivity of the ultrasound transducer using the micro-beamformer of FIG. 5. The simulation diagram shows that an error of the timing does reduce the sensitivity at the steering angle −36° but that does not show any grating lobe Consequently, the ultrasound transducer assemblies 30 according to the present invention provides a reduced sensitivity to timing errors than the transducer assemblies known from the prior art.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An apparatus, comprising:
   an ultrasound transducer array configured to receive acoustic energy, wherein the ultrasound transducer array comprises a first transducer element configured to generate a first signal corresponding to the received acoustic energy and a second transducer element configured to generate a second signal corresponding to the received acoustic energy;
   a first timing element and a second timing element, wherein the first and second timing elements are in communication with the first transducer element and configured to provide different time shifts to the first signal to generate a first shifted signal and a second shifted signal, respectively;
   a third timing element and a fourth timing element, wherein the third and fourth timing elements are in communication with the second transducer element and configured to provide different time shifts to the second signal to generate a third shifted signal and a fourth shifted signal, respectively;
   a first signal combiner in communication with the first and third timing elements and configured to combine the first and third shifted signals to generate a first combined signal;
   a second signal combiner in communication with the second and fourth timing elements and configured to combine the second and fourth shifted signals to generate a second combined signal; and
   an overall combiner configured to combine the first and second combined signals to generate an output signal.

2. The apparatus of claim 1, wherein the first signal combiner, the second signal combiner, and the overall combiner each comprise a signal adder.

3. The apparatus of claim 1, wherein the overall combiner is configured to apply different weights to the first combined signal and the second combined signal.

4. The apparatus of claim 1, further comprising, for each of the first transducer element and the second transducer element, at least one of an amplifier or an attenuator, wherein the at least one of the amplifier or the attenuator is configured to apply gain factors to signals of the respective transducer elements.

5. The apparatus of claim 4, wherein the gain factors comprise different absolute values.

6. The apparatus of claim 1, wherein the first timing element is configured to provide a first fixed time delay and a first relative time shift, wherein the second timing element is configured to provide a second fixed time delay and a second relative time shift.

7. The apparatus of claim 6, wherein the first relative time shift comprises a positive time shift, and wherein the second relative time shift comprises a negative time shift.

8. The apparatus of claim 7, wherein the third timing element is configured to provide a third fixed time delay and a third relative time shift, wherein the fourth timing element is configured to provide a fourth fixed time delay and a fourth relative time shift.

9. The apparatus of claim 8, wherein the third relative time shift comprises a positive time shift, and wherein the fourth relative time shift comprises a negative time shift.

10. The apparatus of claim 8, wherein the third relative time shift comprises a negative time shift, and wherein the fourth relative time shift comprises a positive time shift.

11. The apparatus of claim 6, wherein the first and second relative time shifts comprise different absolute values.

12. The apparatus of claim 1, further comprising:
   a third transducer element of the array configured to provide a third signal; and
   a fifth timing element in communication with the third transducer element such that the third transducer element of the array is in communication with a single timing element, the fifth timing element configured to provide a time shift to the second signal to generate a fifth shifted signal, wherein the fifth timing element is in communication with the first signal combiner.

13. The apparatus of claim 12, wherein the fifth timing element is configured to apply only a fixed time delay.

* * * * *